United States Patent [19]
Pierschbacher et al.

[11] Patent Number: 5,858,972
[45] Date of Patent: Jan. 12, 1999

[54] ANTITHROMBOTIC AGENTS AND METHODS OF USE

[75] Inventors: Michael D. Pierschbacher; Daniel G. Mullen, both of San Diego, Calif.

[73] Assignee: La Jolla Cancer Research Foundation, La Jolla, Calif.

[21] Appl. No.: 585,281

[22] Filed: Jan. 11, 1996

[51] Int. Cl.$^6$ .......................... A61K 38/00; A61K 38/12; C07K 7/50; C07K 7/64

[52] U.S. Cl. ........................ 514/11; 530/317; 530/328

[58] Field of Search .............................. 514/11; 530/317, 530/328

[56] References Cited

FOREIGN PATENT DOCUMENTS

| | | |
|---|---|---|
| 422937 | 4/1991 | European Pat. Off. |
| WO 91/15515 | 10/1991 | WIPO |
| 94/20127 | 9/1994 | WIPO |
| WO 94/25071 | 11/1994 | WIPO |
| WO 95/00544 | 1/1995 | WIPO |
| WO 95/28426 | 10/1995 | WIPO |

OTHER PUBLICATIONS

Gilon et al. Biopolymers, 31, 745–750, Feb. 1991.

Paborsky et al., "A Peptide Derived from a Tissue Factor Loop Region Functions as a Tissue Factor–Factor VIIa Antagonist." *Biochemistry*, 34:153298–15333 (1995).

Barker et al., "Cyclic RGD peptide analogues as antiplatelet antithrombotics." *J. Med. Chem.*, 35:2040–2048 (1992).

Cheng et al., "Design and synthesis of novel cyclic RGD-–containing peptides as highly potent and selective integrin $\alpha_{IIb}\beta_3$ antagonists." *J. Med. Chem.*, 37:1–8 (1994).

Tschopp et al., "Inhibition of coronary artery reocclusion after thrombolysis with an RGD–containing peptide with no significant effect on bleeding time." *Coronary Artery Dis.*, 4:809–817 (1993).

Scarborough et al., "Design of potent and specific integrin antagonists: Peptide antagonists with high specificity for glycoprotein IIb–IIIa." *J. Biol. Chem.*, 268:1066–1073 (1993).

Scarborough et al., "Characterization of the integrin specificities of disintegrins isolated from american pit viper venoms." *J. Biol. Chem.*, 268:1058–1065 (1993).

Collen et al., "Antithrombotic effects and bleeding time prolongation with synthetic platelet GPIIb/IIIa inhibitors in animal models of platelet–mediated thrombosis." *Thrombosis & Haemostasis*, 71:95–102 (1994).

Sims et al., "Effect of platelet activation on the conformation of the plasma membrane glycoprotein IIb–IIIa complex." *J. Biol. Chem.*, 266(12):7345–7352 (1991).

Phillips et al., "The glycoprotein Iib–IIIa complex in platelets and nucleated cells." In: *Platelet Activation*, H. Yamazaki & J.F. Mustard, eds., Academic Press, Toronto, 57–70 (1987).

Pelletier et al., "The activation state of the integrin $\alpha IIb\beta 3$ affects outside–in signals leading to cell spreading and focal adhesion kinase phosphorylation." *J. Biol. Chem.*, 270(30):18133–18140 (1995).

Savage et al., "Modulation of platelet function through adhesion receptors: a dual role for glycoprotein IIb–IIIa(Integrin $\alpha IIb\beta 3$) mediated by fibrinogen and glycoprotein Ib–von Willebrand factor." *J. Biol. Chem.*, 267(16):11300–11306 (1992).

Grzesiak and Pierschbacher, "Shifts in the concentrations of magnesium and calcium in early porcine and rat wound fluids activate the cell migratory response." *J. Clin. Invest.*, 95:227–233 (1995).

Kirchhofer et al., "Calcium as a potential physiological regulator of integrin–mediated cell adhesion." *J. Biol. Chem.*, 266(7):4471–4477 (1991).

*Primary Examiner*—Cecilia J. Tsang
*Assistant Examiner*—Michael Borin
*Attorney, Agent, or Firm*—Campbell & Flores LLP

[57] ABSTRACT

The present invention provides antithrombotic agents useful for the management of cardiovascular disease. The agents of the subject invention are novel cyclic peptides encompassed by the following formula:

$$Y-X_1-X_2-G-D-X_3-X_4-X_5-Z$$

(SEQ ID NO. 1). In the above formula, $X_2$ and $X_3$ are independently a hydrophobic amino acid and $X_4$ is a positively charged amino acid. The $X_1$ and $X_5$ substituents are independently zero to five amino acids. The amino and carboxy terminal amino acids of a given peptide can be modified according to the substituents Y and Z, respectively. The peptides are cyclized through a bridge between the two amino acids with the peptide, excluding G, D and $X_3$ in the formation of the bridge. Peptides encompassed by the above formula can be administered in a suitable physiologically acceptable carrier to therapeutically treat thrombosis and conditions resulting from the development of thrombi. Unexpectedly, the above-described agents have a higher apparent affinity for GP-IIb/IIIa at low calcium concentration, which is typical at the site of a clot, as compared to at higher calcium concentration found elsewhere throughout the whole blood stream.

19 Claims, 3 Drawing Sheets

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( D ) TOPOLOGY: circular     ( i i ) MOLECULE TYPE: peptide     ( x i ) SEQUENCE DESCRIPTION: SEQ ID NO:1:

Xaa  Xaa  Gly  Asp  Xaa  Xaa  Xaa
    1                          5

( 2 ) INFORMATION FOR SEQ ID NO:2:

( i ) SEQUENCE CHARACTERISTICS:

(A) LENGTH: 9 amino acids
                (B) TYPE: amino acid
                (D) TOPOLOGY: circular (i i) MOLECULE TYPE: peptide (i x) FEATURE:
                (A) NAME/KEY: Peptide
                (B) LOCATION: 1
                (D) OTHER INFORMATION: /note= "Amino acid is acetylated at
                        the N- terminal."

(i x) FEATURE:
                (A) NAME/KEY: Peptide
                (B) LOCATION: 7
                (D) OTHER INFORMATION: /note= "Tyr is methylated; (Y-OMe)"

(i x) FEATURE:
                (A) NAME/KEY: Peptide
                (B) LOCATION: 9
                (D) OTHER INFORMATION: /note= "Amino acid is amidated at
                        the C- terminal."

(x i) SEQUENCE DESCRIPTION: SEQ ID NO:2:

Cys  Asn  Pro  Ala  Gly  Asp  Tyr  Arg  Cys
         1                    5

(2) INFORMATION FOR SEQ ID NO:3:

(i) SEQUENCE CHARACTERISTICS:
                (A) LENGTH: 9 amino acids
                (B) TYPE: amino acid
                (D) TOPOLOGY: circular (i i) MOLECULE TYPE: peptide (i x) FEATURE:
                (A) NAME/KEY: Peptide
                (B) LOCATION: 1
                (D) OTHER INFORMATION: /note= "Amino Acid is acetylated at
                        the N- terminal."

(i x) FEATURE:
                (A) NAME/KEY: Peptide
                (B) LOCATION: 4
                (D) OTHER INFORMATION: /note= "Xaa is (Nle)"

(i x) FEATURE:
                (A) NAME/KEY: Peptide
                (B) LOCATION: 7
                (D) OTHER INFORMATION: /note= "Tyr is methylated; (Y-OMe)"

(i x) FEATURE:
                (A) NAME/KEY: Peptide
                (B) LOCATION: 9
                (D) OTHER INFORMATION: /note= "Amino acid is amidated at
                        the C- terminal."

(x i) SEQUENCE DESCRIPTION: SEQ ID NO:3:

Cys  Asn  Pro  Xaa  Gly  Asp  Tyr  Arg  Cys
         1                    5

(2) INFORMATION FOR SEQ ID NO:4:

(i) SEQUENCE CHARACTERISTICS:
                (A) LENGTH: 6 amino acids
                (B) TYPE: amino acid
                (D) TOPOLOGY: circular (i i) MOLECULE TYPE: peptide (i x) FEATURE:
                (A) NAME/KEY: Peptide
                (B) LOCATION: 1
                (D) OTHER INFORMATION: /note= "Xaa is (Nle)"

( i x ) FEATURE:
    ( A ) NAME/KEY: Peptide
    ( B ) LOCATION: 4
    ( D ) OTHER INFORMATION: /note= "Tyr is methylated; (Y-OMe)"

( i x ) FEATURE:
    ( A ) NAME/KEY: Peptide
    ( B ) LOCATION: 6
    ( D ) OTHER INFORMATION: /note= "Amino acid is amidated at the C- terminal."

( x i ) SEQUENCE DESCRIPTION: SEQ ID NO:4:

Xaa Gly Asp Tyr Arg Glu
 1                5

( 2 ) INFORMATION FOR SEQ ID NO:5:

( i ) SEQUENCE CHARACTERISTICS:
    ( A ) LENGTH: 9 amino acids
    ( B ) TYPE: amino acid
    ( D ) TOPOLOGY: linear   ( i i ) MOLECULE TYPE: peptide   ( i x ) FEATURE:
    ( A ) NAME/KEY: Peptide
    ( B ) LOCATION: 1
    ( D ) OTHER INFORMATION: /note= "Amino acid is acetylated at the N- terminal."

( i x ) FEATURE:
    ( A ) NAME/KEY: Peptide
    ( B ) LOCATION: 7
    ( D ) OTHER INFORMATION: /note= "Tyr is methylated; (Y-OMe)"

( i x ) FEATURE:
    ( A ) NAME/KEY: Peptide
    ( B ) LOCATION: 9
    ( D ) OTHER INFORMATION: /note= "Amino acid is amidated at the C- terminal."

( x i ) SEQUENCE DESCRIPTION: SEQ ID NO:5:

Cys Asn Pro Ala Gly Asp Tyr Arg Cys
 1                    5

( 2 ) INFORMATION FOR SEQ ID NO:6:

( i ) SEQUENCE CHARACTERISTICS:
    ( A ) LENGTH: 9 amino acids
    ( B ) TYPE: amino acid
    ( D ) TOPOLOGY: linear   ( i i ) MOLECULE TYPE: peptide   ( i x ) FEATURE:
    ( A ) NAME/KEY: Peptide
    ( B ) LOCATION: 1
    ( D ) OTHER INFORMATION: /note= "Amino acid is acetylated at the N- terminal."

( i x ) FEATURE:
    ( A ) NAME/KEY: Peptide
    ( B ) LOCATION: 4
    ( D ) OTHER INFORMATION: /note= "Xaa is (Nle)"

( i x ) FEATURE:
    ( A ) NAME/KEY: Peptide
    ( B ) LOCATION: 7
    ( D ) OTHER INFORMATION: /note= "Tyr is methylated; (Y-OMe)"

( i x ) FEATURE:
    ( A ) NAME/KEY: Peptide
    ( B ) LOCATION: 9
    ( D ) OTHER INFORMATION: /note= "Amino acid is amidated at the C- terminal."

( x i ) SEQUENCE DESCRIPTION: SEQ ID NO:6:

Cys  Asn  Pro  Xaa  Gly  Asp  Tyr  Arg  Cys
 1                     5

( 2 ) INFORMATION FOR SEQ ID NO:7:

( i ) SEQUENCE CHARACTERISTICS:
      ( A ) LENGTH: 6 amino acids
      ( B ) TYPE: amino acid
      ( D ) TOPOLOGY: linear    ( i i ) MOLECULE TYPE: peptide    ( x i ) SEQUENCE DESCRIPTION: SEQ ID NO:7:

Gly  Arg  Gly  Asp  Ser  Pro
 1                     5

( 2 ) INFORMATION FOR SEQ ID NO:8:

( i ) SEQUENCE CHARACTERISTICS:
      ( A ) LENGTH: 9 amino acids
      ( B ) TYPE: amino acid
      ( D ) TOPOLOGY: circular    ( i i ) MOLECULE TYPE: peptide    ( i x ) FEATURE:
      ( A ) NAME/KEY: Peptide
      ( B ) LOCATION: 1
      ( D ) OTHER INFORMATION: /note= "Amino acid is acetylated at
         the N- terminal."

( i x ) FEATURE:
      ( A ) NAME/KEY: Peptide
      ( B ) LOCATION: 7
      ( D ) OTHER INFORMATION: /note= "Tyr is methylated; (Y-OMe)"

( i x ) FEATURE:
      ( A ) NAME/KEY: Peptide
      ( B ) LOCATION: 9
      ( D ) OTHER INFORMATION: /note= "Amino acid is amidated at
         the C- terminal."

( x i ) SEQUENCE DESCRIPTION: SEQ ID NO:8:

Cys  Asn  Pro  Arg  Gly  Asp  Tyr  Arg  Cys
 1                     5

( 2 ) INFORMATION FOR SEQ ID NO:9:

( i ) SEQUENCE CHARACTERISTICS:
      ( A ) LENGTH: 5 amino acids
      ( B ) TYPE: amino acid
      ( D ) TOPOLOGY: unknown    ( i i ) MOLECULE TYPE: peptide    ( x i ) SEQUENCE DESCRIPTION: SEQ ID NO:9:

Xaa  Gly  Asp  Xaa  Xaa
 1                 5

( 2 ) INFORMATION FOR SEQ ID NO:10:

( i ) SEQUENCE CHARACTERISTICS:
      ( A ) LENGTH: 6 amino acids
      ( B ) TYPE: amino acid
      ( D ) TOPOLOGY: unknown    ( i i ) MOLECULE TYPE: peptide    ( x i ) SEQUENCE DESCRIPTION: SEQ ID NO:10:

Xaa  Xaa  Gly  Asp  Xaa  Xaa (2) INFORMATION FOR SEQ ID NO:11:

(i) SEQUENCE CHARACTERISTICS:
        (A) LENGTH: 6 amino acids
        (B) TYPE: amino acid
        (D) TOPOLOGY: unknown     (ii) MOLECULE TYPE: peptide     (xi) SEQUENCE DESCRIPTION: SEQ ID NO:11:

Xaa  Gly  Asp  Xaa  Xaa  Xaa
     1                     5

ANTITHROMBOTIC AGENTS AND METHODS OF USE

BACKGROUND OF THE INVENTION

1. Field of the Invention

The present invention relates generally to the field of thrombosis and, more specifically, to novel antithrombotic agents and methods of using the same.

2. Background Information

Cardiovascular disease is a devastating problem in the United States and worldwide. Statistics bear this out. The American Heart Association reports there were 1.5 million myocardial infarctions in the U.S. in 1991 and another 1.7 million in Europe. In 1990, in the U.S. alone, there were 779,000 hospital admissions for unstable angina, up three times as many from 1983. Angioplasty was performed on about 400,000 patients in the U.S. in 1994 and in Europe an additional 177,000 patients underwent the same treatment. In addition, approximately 500,000 U.S. patients suffer strokes each year.

Cardiovascular disease comprises four main categories: (1) coronary artery disease which leads to myocardial infarction or heart attack, (2) cerebrovascular disease causing strokes, (3) peripheral artery disease which leads to ischemia and (4) venous thrombosis, blood clots in deep veins. A common feature of these vascular diseases is thrombosis, clotting within blood vessels, which results in loss of blood flow to vital tissues and organs. The formation of a blood clot within a blood vessel, thrombosis, and the resulting loss of circulating blood can cause tissue damage and, if untreated, in many cases death.

Thrombus formation is dependent upon platelet aggregation. The interaction of blood platelets with the subendothelial surface of injured blood vessels and with other platelets is a major factor in the course of development of thrombi. Platelet aggregation is dependent upon the binding of fibrinogen and other serum proteins to the glycoprotein GP-IIb/IIIa complex on the platelet plasma membrane, thus cross-linking one platelet to another. GP-IIb/IIIa is a member of a large family of cell adhesion receptors known as integrins. The GP-IIb/IIIa integrin is found only on the surface of platelets and blocking it prevents platelets from aggregating and forming blood clots. Inhibition of GP-IIb/IIIa receptor binding and, therefore, of platelet aggregation is sufficient for the prevention of thrombosis.

Currently, there are various products available for preventing (aspirin, Ticlid®, ReoPro™, dipyridamole, heparin) or dissolving blood clots (tissue-plasminogen activator (t-PA) and streptokinase). These products either destroy or remove platelets or target fibrin in an attempt to eliminate the clot. However, each has the potential serious side effect of causing prolonged bleeding. Moreover, the effects of these products are only slowly reversible.

Known GP-IIb/IIIa antagonists include antibodies which bind irreversibly to the receptor, synthetic peptides incorporating either the RGD or KGD amino acid sequences, both of which sequences are recognized by the GP-IIb/IIIa receptor, and peptide mimetics which antagonize GP-IIb/IIIa in a manner similar to the peptides. However, most, if not all, of these compounds also cause elevated bleeding.

To minimize bleeding complications, it is important to create molecules which have a higher affinity for GP-IIb/IIIa at low calcium concentrations, which is the condition at the site of clot formation, as compared to the normal, higher physiological calcium concentration found in the systemic blood supply. By inhibiting GP-IIb/IIIa at the site of a clot where calcium concentration is low, and not throughout the whole blood stream, unacceptable bleeding may be controlled when optimal doses of a drug are used. Put another way, to reduce or eliminate bleeding complications, it is important to inhibit GP-IIb/IIIa mediated platelet aggregation only at the clot site under low calcium concentration, and not in the rest of the blood stream where the calcium concentration is higher and GP-IIb/IIIa is necessary for platelet adhesion and spreading. Thus, there exists a need for GP-IIb/IIIa receptor antagonists which have a higher affinity for GP-IIb/IIIa at low calcium concentration than at physiological calcium concentration. The present invention satisfies this need and provides related advantages as well.

SUMMARY THE INVENTION

The invention provides antithrombotic agents which are novel cyclic peptides having the general structure Y-$X_1$-$X_2$-G-D-$X_3$-$X_4$-$X_5$-Z (SEQ ID NO. 1). Within this genus, $X_2$, $X_3$, and $X_4$ are each a single amino acid which meets a specific physiochemical characteristic. More specifically, $X_2$ and $X_3$ are independently a hydrophobic amino acid and $X_4$ is a positively charged amino acid. The $X_1$ and $X_5$ substituents of the above genus can be absent or present. If either or both $X_1$ and $X_5$ are present, they are independently substituted by one to five amino acids. The Y and Z substituents represent various possible modifications to the amino and carboxy terminal amino acids, respectively. Finally, the peptides are cyclized through a bridge between two amino acids, excepting the G, D and $X_3$ amino acids in the formation of a bridge.

Peptides encompassed by the above formula can be administered in a suitable physiologically acceptable carrier to therapeutically treat thrombosis and conditions resulting from the development of thrombi.

BRIEF DESCRIPTION OF THE DRAWINGS

FIGS. 2a–2c provide the percentage of platelet aggregation also in citrated and heparinized plasma in the presence of control peptide GRGDSP (SEQ ID NO. 7; FIG. 2a) and two representative peptides of the present invention, Ac-CNPAGD(Y-OMe)RC-$NH_2$ (SEQ ID NO.2; FIG. 2b) and Ac-CNP(Nle)GD(Y-OMe)RC-$NH_2$ (SEQ ID NO. 3; FIG. 2c).

DETAILED DESCRIPTION OF THE INVENTION

Prevention of thrombus formation is critical to the management of cardiovascular diseases. The present invention provides antithrombotic agents useful for such management. The agents of the subject invention are novel cyclic peptides encompassed by the following formula:

(SEQ ID NO. 1). In the above formula, the substituents flanking the GD dipeptide, $X_2$ and $X_3$, are each a single hydrophobic amino acid. The $X_4$ variable is a positively charged amino acid. The $X_1$ and $X_5$ substituents can individually be absent or present. If either or both $X_1$ and $X_5$ are present, they are independently substituted by one to five amino acids. The amino and carboxy terminal amino acids of a given peptide can be modified according to the substituents Y and Z, respectively. The peptides are cyclized through a bridge between two amino acids within the sequence, excluding the G, D and $X_3$ amino acids.

Unexpectedly, the agents of the invention have affinity for GP-IIb/IIIa and, moreover, they have a higher apparent affinity for GP-IIb/IIIa at low calcium concentration, which is typical at the site of a clot, compared to GP-IIb/IIIa at higher, physiological calcium concentration as found elsewhere throughout the blood stream. Thus, what is exceptional about the GP-IIb/IIIa antagonists of the present invention is that they inhibit platelet aggregation but not significantly impair other normal platelet functions, thereby circumventing bleeding complications common to other antithrombotics.

The one-letter and three-letter abbreviations for amino acids and derivatives thereof used herein are as follows:

| A | Ala | Alanine |
|---|---|---|
|   | α-ABA | α-Amino isobutyric acid |
| R | Arg | Arginine |
| N | Asn | Asparagine |
| D | Asp | Aspartic acid |
|   | Cha | Cyclohexyl-alanine |
|   | Chg | Cyclohexyl-glycine |
|   | Cit | Citrulline |
| C | Cys | Cysteine |
| Q | Gln | Glutamine |
| E | Glu | Glutamic acid |
| G | Gly | Glycine |
|   | t-butylG | tert-butyl-glycine |
| H | His | Histidine |
|   | homoPhe | homoPhenylalanine |
|   | homoArg | homoArginine |
| I | Ile | Isoleucine |
| L | Leu | Leudine |
| K | Lys | Lysine |
| M | Met | Methionine |
|   | Mpa | β-Mercaptopropionic acid |
|   | Msa | β-[(methylsulfonyl)amino]alanine |
|   | 1-Nal | β-(1-naphthyl) Ala |
|   | 2-Nal | β-(2-naphthyl)Ala |
|   | Nap | naphthyl-alanine analogues |
|   | Nle | Norleucine |
|   | Npg | neopentyl-glycine |
|   | Nve | Norvaline |
|   | O-n-butyl-Tyr | O-n-butyl-tyrosine |
|   | O-n-hexyl-Tyr | O-n-hexyl-tyrosine |
|   | Orn | Ornithine |
|   | P-amino-Phe | para-amino-phenylalanine |
|   | Pas | 6,6-Cyclopentamethylene-2-Aminosuberic acid analogues |
|   | Psa | β-[(phenylsulfonyl)amino]alanine |
|   | Pen | Penicillamine |
| F | Phe | Phenylalanine |
|   | p-chloro-Phe | para-chloro-phenylalanine |
|   | Phg | phenylglycine |
|   | p-iodo-Phe | para-iodo-phenylalanine |
|   | Pmc | amino-β₁, β-pentamethylene-β-mercaptopropionic acid |
|   | Pmp | β₁,β-pentamethylene-β-mercaptopropionic acid analogues |
|   | P-nitro-Phe | para-nitro-phenylalanine |
| P | Pro | Proline |
| S | Ser | Serine |
|   | SuccAla | Succinyl-alanine |
| T | Thr | Threonine |
|   | Tfsa | β-[(trifluoromethylsulfonyl)amino]alanine |
| W | Trp | Tryptophan |
| Y | Tyr | Tyrosine |
|   | Tyr-OMe | O-methyl-tyrosine (Y-OMe) |
|   | Tyr-OEt | O-ethyl-tyrosine (Y-OEt) |
|   | 3,5-diiodo-Tyr | 3,5-diiodo-tyrosine |
| V | Val | Valine |

As used herein, the term "hydrophobic amino acid" is intended to include naturally-occurring hydrophobic amino acids, including Ala, Val, Ile, Leu, Phe, Tyr and Trp as well as non-naturally-occurring hydrophobic amino acids, including the D-form of the hydrophobic amino acids, amino acid derivatives and amino acid mimics, which are non-polar. Hydrophobic amino acid derivatives and mimetics useful in the invention can have a range of structural types and hydrophobicities. Examples of such include, but are not limited to, Nle, Nve, Cha, Nap, 2-Nal, Cit. Tyr derivatives, Phe derivatives and Trp derivatives. Examples of additional hydrophobic amino acids include Chg, t-butylG, Msa, Npg, Psa, Tfsa and 1-Nal. Examples of Tyr derivatives include Tyr-OMe, Tyr-OEt, O-n-hexyl-Tyr, O-n-butyl-Tyr, 3,5-diiodo-Tyr and the like. Examples of Phe derivatives include p-chloro-Phe, homoPhe, p-nitro-Phe, Phg, p-iodo-Phe, p-amino-Phe and the like. Tryptophan derivatives are, for example, Trp amino acid analogs with a substituted indole ring, substituted with, for example, one or more halogen atoms including iodo, chloro, fluoro, and bromo atom(s), and/or one or more alkyl groups, such as methyl, ethyl, and the like.

In one embodiment of the invention, $X_2$ and $X_3$ are independently each a hydrophobic amino acid. In another embodiment of the invention, the hydrophobic amino acid of either, or both, $X_2$ and $X_3$ is selected from the group consisting of Ala, Val, Ile, Leu, Phe, Tyr, Trp, a Tyr derivative, a Phe derivative, a Trp derivative, Nle, Nve, Cha, Nap, 2-Nal and Cit, with the exception that the amino acid in the $X_2$ position cannot be positively charged. In yet another embodiment, either or both $X_2$ and $X_3$ is Ala, Val, Ile, Leu, Phe, Tyr, Trp, Nle, Nve, a Tyr derivative or a Phe derivative.

More specifically as to $X_2$, and in yet another embodiment of the invention, $X_2$ is Ala, Val, Ile, Leu, Phe, Tyr, Trp, Nve, Nle, Cha or Nap. In a preferred embodiment, $X_2$ is Ala, Val, Ile, Leu, Phe, Tyr, Trp, Nve, or Nle. In a more preferred embodiment, $X_2$ is Ala, Leu or Nle and, more preferably Leu or Nle.

More specifically as to $X_3$ and in yet another embodiment of the invention, $X_3$ is Phe or a derivative of Phe, including homoPhe, p-chloro-Phe, p-nitro-Phe, Phg, p-iodo-Phe, p-amino-Phe and Tyr or a derivative of Tyr, including Tyr-OMe, Tyr-OEt, O-n-butyl-Tyr, O-n-hexyl-Tyr, 3,5-diiodo-Tyr, as well as Trp, 2-Nal, Cha and Cit. In a preferred embodiment, $X_3$ is Phe, a derivative of Phe, Tyr, a derivative of Tyr or Trp. In a more preferred embodiment, $X_3$ is a derivative of Tyr, and more preferably, Tyr-OMe.

The amino acids arginine and lysine are not, and could not be, characterized as hydrophobic amino acids. They are positively charged amino acids. Therefore, R and K are not encompassed within the definition of "a hydrophobic amino acid." It is not intended that R and K, or derivatives thereof, fall within this definition or could be substituted for either $X_2$ or $X_3$. It should be emphasized that $X_2$ by the formula and definitions provided cannot be R, K, or any other positively charged amino acid derivative thereof. The peptides of the present invention are not intended to contain the well known RGD or KGD tripeptide sequence. In fact, the peptides of the present invention provide unexpectedly superior properties as compared to RGD-containing peptides in their greater separation in affinity for the GP-IIb/IIIa receptor at low calcium concentrations relative to in higher calcium concentration. Comparative data provided in the ensuing Examples evidences this superiority.

As used herein, the term "positively charged amino acid" refers to those amino acids which occur in nature, including Arg, Lys and His, and the D-form of these naturally-occurring amino acids as well as amino acid derivatives and amino acid mimics, which are positively charged. Examples of additional positively charged amino acids include, but are not limited to, Orn and homoArg.

In a preferred embodiment of the present invention, the positively charged amino acid of $X_4$ is Arg, Lys, His, Orn or homArg. In a more preferred embodiment, $X_4$ is Arg or Lys, and more preferably, Arg.

The variables $X_1$ and $X_5$ are, independently, zero to five amino acids. When present and between one and five amino acids, $X_1$ and $X_5$ can contain any naturally-occurring or non-naturally-occurring amino acids, including the D-form of the amino acids, amino acid derivatives and amino acid mimics, so long as the desired function and activity of the peptide is maintained.

The choice of including an (L)- or a (D)-amino acid in the peptides of the present invention depends, in part, on the desired characteristics of the peptide. For example, the incorporation of one or more (D)-amino acids can confer increased stability on the peptide and can allow a peptide to remain active in the body for an extended period of time. The incorporation of one or more (D)-amino acids can also increase or decrease the pharmacological activity of the peptide as determined, for example, using the assays described in Example II below, or other assays described below or known to those of skill in the art.

The length of the peptides will depend on the substitution for $X_1$ and $X_5$. The peptides must at least comprise $X_2GDX_3X_4$ (SEQ ID NO. 9) and, therefore, are at least 5 amino acids, or the equivalent, in length. At the upper limit and based on the above formula, the cyclic peptides can be as long as 15 amino acid residues. It should, however, be appreciated to those of skill in the art that the addition of one to a few amino acids to increase the peptide length beyond 15 residues could likely yield similar activity and, therefore, would not depart from the spirit and concept of the present invention. Such will depend on the ability to retain a cyclic conformation as compared to a linear structure. As shown in the ensuing Examples, cyclization provides the peptides of the present invention with superior properties over their linear counterparts. The length of the peptides will also depend on whether either or both $X_1$ and $X_5$ are present. For example, peptides encompassed within the present invention, include those of the formulas Y-$X_1$-$X_2$-GD-$X_3$-$X_4$ (SEQ ID NO. 10) and $X_2$-GD-$X_3$-$X_4$-$X_5$-Z (SEQ ID NO. 11). The length of the peptides are preferably less than about 10 amino acids, and more preferably, less than about 7 amino acids in length.

As used herein, the terms "amino acid mimic" and "mimetic" mean an amino acid analog or non-amino acid moiety that has the same or similar functional characteristic of a given amino acid. For instance, an amino acid mimic of a hydrophobic amino acid is one which is non-polar and retains hydrophobicity, generally by way of containing an aliphatic chemical group. By way of further example, an arginine mimic can be an analog of arginine which contains a side chain having a positive charge at physiological pH, as is characteristic of the guanidinium side chain reactive group of arginine.

In addition, modifications to the peptide backbone and peptide bonds thereof are also encompassed within the scope of amino acid mimic or mimetic. Such modifications can be made to the amino acid, derivative thereof, non-amino acid moiety or the peptide either before or after the amino acid, derivative thereof or non-amino acid moiety is incorporated into the peptide. What is critical is that such modifications mimic the peptide backbone and bonds which make up the same and have substantially the same spacial arrangement and distance as is typical for traditional peptide bonds and backbones. An example of one such modification is the reduction of the carbonyl(s) of the amide peptide backbone to an amine. A number of reagents are available and well known for the reduction of amides to amines such as those disclosed in Wann et al., *JOC,* 46:257 (1981) and Raucher et al., *Tetrahedron. Lett.,* 21:14061 (1980), both of which are incorporated herein by reference. An amino acid mimic is, therefor, an organic molecule that retains the similar amino acid pharmacophore groups as is present in the corresponding amino acid and which exhibits substantially the same spatial arrangement between functional groups.

The substitution of amino acids by non-naturally occurring amino acids and amino acid mimics as described above can enhance the overall activity or properties of an individual peptide based on the modifications to the backbone or side chain functionalities. For example, these types of alterations to the specifically described amino acid substituents and exemplified peptides can enhance the peptide's stability to enzymatic breakdown and increase biological activity. Modifications to the peptide backbone similarly can add stability and enhance activity.

As indicated by the Y and Z substituents of the above generic formula, the peptides of the present invention can be modified at either or both the amino or carboxy terminus. Methods for modifying the termini are well known in the art. Modifications for the amino terminus ("Y") include, for example, COCH$_3$ ("Ac"), CO-alkyl, an alkyl group, CH$_2$PH, COPh, COOCH$_2$Ph or COO-alkyl. Modifications for the carboxy terminus ("Z") include, for example, NH$_2$, NH-NH$_2$, O-alkyl, SH, S-alkyl, NH-alkyl or NHCH$_2$PH. The abbreviation "Ph" indicates a "phenyl" group (C$_6$H$_5$). The terms "alkyl" or "alkyl group" mean a C$_1$ to C$_6$ alkyl, including such radicals as methyl, ethyl, n-propyl, isopropyl, n-butyl, sec-butyl, tert-butyl, amyl, hexyl and the like. A preferred alkyl is methyl.

Above, and in the exemplified peptides, "Ac" indicates an acetyl group at the amino terminus and "NH$_2$" an amide group at the carboxy terminus. Peptides can be manipulated, for example, while still attached to a resin to obtain N-terminal modified agents such as an acetylated peptide or can be removed from the resin using hydrogen fluoride or an equivalent cleaving reagent and then modified. Compounds synthesized containing the C-terminal carboxy group (Wang resin) can be modified after cleavage from the resin, or in some cases, prior to solution phase synthesis. Methods for acetylation of the amino terminus and for amidation of the carboxy terminus as well as those for any of the other above-described modifications are well known in the art.

Any of the above described embodiments of $X_1$, $X_2$, $X_3$, $X_4$, $X_5$, Y and Z can be combined, in any combination, to arrive at yet further embodiments of the present invention than those specific combinations identified above and in the claims.

The peptides of the present invention are cyclic peptides which are cyclized through a bridge between two amino acids of a given peptide sequence, not including G, D or $X_3$ within these two amino acids. As used herein, the term "cyclic peptide" refers to a peptide having an intramolecular bond between the two amino acids forming the bridge within a given peptide. The intramolecular bond includes, but is not limited to, backbone to backbone, side-chain to backbone and side-chain to side-chain cyclizations. An example of a backbone to backbone cyclization is a bridge formed between the amino group of the amino terminus and the carboxylic acid of the carboxy terminus. Examples of a side-chain to side-chain cyclization include, for instance, disulfide bridges formed through cysteine residues or other sulfur containing amino acids capable of forming such bridges or, alternatively, a bridge formed between the side chain of a basic amino acid, such as Lys, and the side chain of an acidic amino acid, such as Glu. Various other amino acid and derivatives thereof and the like can participate in such bonds, including, for example, Cys, Pen, Mpa, Pmp, Pmp analogues, Pas, Pmc and Pmc analogues.

As used herein, the term "bridge" refers to a chemical bond between two amino acids, amino acid derivatives or mimetics in a peptide other than the amide bond, or the like, by which the backbone of the peptide is formed unless the amide bond cyclizes the peptide to form a lactam, as in the case of (Nle)GD(Y-OMe)RE-NH$_2$ (SEQ ID NO. 4). The bridge within a specifically described peptide is identified by underlining ().

As previously stated, the peptides of the present invention are cyclized through a bridge between two of the amino acids within a given peptide sequence, so long as those amino acids are not the G, D or $X_3$ amino acids. In other words, the G, D and $X_3$ amino acids are not involved in the "formation of the bridge," meaning these amino acids do not contribute to the chemical bond of the bridge. The peptide, however, can be cyclized through a bridge between any two of the other amino acids present in a given peptide. Therefore, a peptide can be cyclized through a bridge between the two amino acids, collectively, $X_1$ and $X_5$, $X_1$ and $X_4$, $X_2$ and $X_5$, and $X_2$ and $X_4$.

The cyclization can be, but does not have to be, between the two terminal amino acids of a given peptide. The "two terminal amino acids" means the amino acid at the amino terminus and the amino acid at the carboxy terminus of a given peptide sequence. Which amino acids are at the amino and carboxy termini will depend on the selections for $X_1$, $X_2$, $X_4$ and $X_5$. For example, where $X_1$ and $X_5$ are both absent, $X_2$ and $X_4$ will be the amino and carboxy terminus, respectively, and, therefore, the peptide will be cyclized through a bridge between $X_2$ and $X_4$. It is important, however, that the side chains of $X_2$ and $X_4$ remain present in the peptides of the present invention and, therefore, any bridge between the $X_2$ and $X_4$ amino acids will be a backbone to backbone bridge through the amino and carboxy termini.

When the cyclization is formed through a bridge between amino acids other than the two terminal amino acids, the bridge can be between one terminal amino acid, amino or carboxy, and one non-terminal amino acid or, alternatively, the bridge can be between two non-terminal amino acids. A "non-terminal amino acid" is one which has one or more additional amino acids to either its amino or carboxy side of the peptide chain. An example of a peptide having a bridge between one terminal amino acid and one non-terminal amino acid is where $X_1$ is absent, making $X_2$ a terminal amino acid involved in the cyclization, and $X_5$ is three amino acids in length, the middle amino acid being Glu which bonds through a bridge to $X_2$. An example of a bridge between two non-terminal amino acids is where $X_1$ and $X_5$ each are two to five amino acids in length, one of which such amino acids within $X_1$ and $X_5$, but not the terminal amino acid, is an amino acid capable of forming a bridge to cyclize the peptide, such as, for example, Cys, Pen, Mpa, Pmp, Pmc and Pas.

The peptides of the present invention can be synthesized by any of the suitable methods well known in the art including methods of chemical synthesis. For example, the linear sequence is synthesized using commercially available automated peptide synthesizers such as those manufactured by Applied Biosystems, Inc., Foster City, Calif. Peptides can be synthesized using amino acids or amino acid analogs, the active groups of which are protected as necessary using, for example a t-butyldicarbonate (t-Boc) group or a fluorenyl-methoxy carbonyl (Fmoc) group. Amino acids and amino acid analogs can be purchased commercially (Sigma Chemical Co.; Advanced Chemtec) or synthesized using methods known in the art. Peptides synthesized using the solid phase method can be attached to resins, including 4-methylbenzhydrylamine (MBHA), 4-(oxymethyl) phenylacetamido methyl and 4-(hydroxymethyl) phenoxymethylcopoly(styrene-1% divinylbenzene) (Wang resin), all of which are commercially available, or using other resins well known in the art. The material so synthesized can be cleaved, precipitated and further purified, for example by high performance liquid chromatography (HPLC). Although a purity of greater than 95 percent for the synthesized peptide is generally desirable, lower purity may be acceptable.

The synthesized peptide is cyclized using methods well known in the art. Cyclization can be achieved where the peptides contain two sulphur-containing amino acids, or other moieties through a disulfide bond. Examples of useful sulphur-containing moieties are Cys and Pen and Pmp. Alternatively, cyclization can be accomplished through the formation of a peptide bond or alkyl bridge structures using, for example, Pas. Where the residues contain sulfhydryls, a disulfide bridge can be formed by oxidizing a dilute aqueous solution of the peptides with $K_3[F_e(CN)_6]$. Other residues, such as the chemical moieties Pmp and Pas, can create a bridging structure through a disulfide bond between Pmp and Pmp or Cys (or similar structures) and an amide bond between Pas and an amino moiety (or similar structures). Other means of cyclizing, which are known in the art, can also be utilized.

The cyclized peptides of the present invention can also be prepared by forming a peptide bond between non-adjacent amino acid residues. As used herein, the term "peptide bond" or "peptide linkage" refers to an amide linkage between a carboxyl group of one amino acid and the α-amino group of another amino acid.

Side-chain to side-chain cyclizations can be performed by using $N^\alpha$-Boc-amino acids together with OFm/Fmoc side-chain protection for Asp and Lys residues as described by Felix et al., *Int. J. Peptide Protein Res.*, 31:231 (1988), which is incorporated herein by reference. Alternatively, side-chain to backbone cyclizations can be performed using this procedure.

Backbone to backbone cyclizations can be performed in solution on side chain protected peptides. Briefly, linear side chain protected peptides are synthesized on O-chlorotrityl resin (Barlos et al., *Tetrahedron Lett.*, 30:3947 (1989)), using $N^\alpha$-Fmoc amino acids. After assembly of the sequence on the resin, the $N^\alpha$-Fmoc is removed and the side chain protected peptide is cleaved from the O-chlorotrityl resin with acetic acid. After removal of the acetic acid by rotary evaporation, the peptide is cyclized in solution with the BOP reagent. The solvent is removed by rotary evaporation and the side chain protection then is removed by treatment with trifluoroacetic acid to provide the backbone to backbone cyclic peptide.

Alternative methods of making cyclized peptides are disclosed, for example, in WO 91/01331 entitled "SMALL CYCLIC PEPTIDE AGGREGATION INHIBITORS," published 7 Feb. 1991. As described therein, for example, Bromoacetyl-Gly-Arg(g-2,2,5,7,8-pentamethylchroman-β-sulfonyl)-Gly-Asp(beta-t-butyl)-Cys(S-triphenylmethyl)-O-(polymer resin) can be prepared using standard solid phase peptide synthesis utilizing Fmoc protecting group chemistry on a p-alkoxybenzyl alcohol resin. Repeated treatment of the resin bound peptide with a 1% solution of trifluoroacetic acid in dichloromethane results in cleavage of the S-triphenylmethyl group as evidenced by the bright yellow of the solution. Treatment is continued until dissipation of the yellow color (ca. 1.5 L of the cleavage solution is required per gram of resin bound peptide). After complete cleavage of the S-triphenylmethyl group, the resin bound peptide is washed several times with a 5% solution of N-methylmorpholine in N,N-dimethylacetamide and then shaken in pure N,N-dimethylacetamide for 12 hours to complete the cyclization. Treatment of the cyclized resin bound peptide with trifluoroacetic acid containing (v/v) 1% phenol, 1% anisole and 1% ethanedithiol effects concomitant cleavage of the remaining protective groups and cleavage of the desired product from the resin, which can then be purified, for example by HPLC using a 4.6 mm×250 mm column containing 10 micron, 300 Angstrom pore size C-18 packing. The elution of the column was with an acetonitrile 0.1% aqueous trifluoroacetic acid gradient going from 0%–40% acetonitrile linearly over 80 minutes.

The invention also provides a composition of matter comprising a cyclic peptide encompassed by the above formula. The peptides can be combined with a physiologically acceptable carrier to form a composition useful for the prevention and treatment of thrombosis and conditions resulting therefrom. Physiologically acceptable carriers are well known in the art and include aqueous solutions such as physiologically buffered saline or other buffers or solvents or vehicles such as glycols, glycerol, oils such as olive oil or injectable organic esters. A physiologically acceptable carrier can contain acceptable compounds that act, for example, to stabilize the antithrombotic agent, increase the absorption of the peptide, or extend the half-life in the circulation. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a physiologically acceptable carrier depends, for example, on the route of administration and on the particular physiochemical characteristic of the specific antithrombotic peptide.

Preventing platelet aggregation is essential to blocking the clotting associated with myocardial infarction, angina, stroke, angioplasty and bypass surgery. A particularly effective prevention of platelet aggregation is to antagonize the GP-IIb/IIIa receptor, at low calcium concentration, which is typical of wound site conditions. The peptides of the present invention can be utilized to prevent or effectively eliminate, and thereby treat, thrombosis and thrombotic conditions by administering to a mammal exhibiting thrombosis or a thrombotic condition a therapeutically effective amount of the peptide in a suitable physiologically acceptable carrier. A "thrombotic condition" means any condition pertaining to or affected with thrombosis and includes such conditions as stroke, myocardial infarction, unstable angina, vascular graft occlusion and abrupt reclosure following angioplasty. Effective amounts will be 0.1 to 50 mg/kg body weight, preferably about 0.1 to 5 mg/kg body weight. Appropriate effective amounts can be easily determined by those skilled in the art. The peptide can be administered in a variety of ways, as for example, by infusion or injection. Length of treatment can be determined by monitoring the functionality of platelets.

Specific peptides having the desired characteristics of the present invention include the following:

Ac-<u>C</u>NPAGD(Y-OMe)R<u>C</u>-NH$_2$ (SEQ ID NO. 2),
Ac-<u>C</u>NP(Nle)GD(Y-OMe)R<u>C</u>-NH$_2$ (SEQ ID NO. 3), and
(Nle)GD(Y-OMe)RE-NH$_2$ (SEQ ID NO. 4).

Although the invention will be described with reference to these specific peptides it is understood that functional equivalents known to those skilled in the art can be substituted for the given sequence without departing from the spirit of the invention. Peptides having sequences other than those specifically identified herein are also included in the invention provided they exhibit the requisite functional criteria; peptides which have high antithrombotic activity and which have a higher apparent affinity for the GP-IIb/IIIa receptor at low calcium concentrations as compared to physiological calcium concentrations.

Such peptides once synthesized can be tested for antithrombotic activity using, for example, the platelet aggregation assays described in Example II. In addition, one can test the instant peptides in any of the commonly used protocols and procedures for assessing antithrombotic agents against various thrombotic conditions. For instance, the Folts model (Steinmetz et al., *Cardiovascular Res., Genentech, Inc.*, (1993)), which measures incidence of cyclic flow reductions, can be used to study the effectiveness of an agent in eliminating platelet-rich thrombi formed after coronary artery damage and vessel stricture.

Known procedures for assessing vascular graft occlusion include the Collen dog eversion graft model, which mimics a natural graft situation (Collen et al., *Thrombosis and Haemostasis*, 71(1) :95–102 (1994)), and the Connolly baboon model, which mimics the formation of platelet aggregates on a synthetic substrate (Mazur et al., *J. Lab. Clin. Med.*, 124(4):589–598 (1994)). Other models include the Collen hamster model (Collen et al., supra), the Lucchesi dog model (Tschopp et al., *Coronary Artery Disease*, 4:809–817 (1993)) and the Gold dog model (Yasuda et al., *Cardiovascular Res., Genentech, Inc.*, (1993)) as well as others well known in the field. Thus, one skilled in the art can use the teachings of the invention to make and test a variety of peptides having the generic structures described herein. One skilled in the art will be able to use such functional equivalents to practice the invention described herein. Thus, the following Examples are intended only to illustrate, but not limit, the invention.

EXAMPLE I

Peptide Synthesis

This example provides methods for chemically synthesizing peptides of the present invention.

A. Synthesis of cyclic peptides having disulfide bonds:

Peptides cyclized through disulfide bridges, including Ac-<u>C</u>NPAGD(Y-OMe)R<u>C</u>-NH$_2$ (SEQ ID NO. 2) and Ac-<u>C</u>NP(Nle)GD(Y-OMe)R<u>C</u>-NH$_2$ (SEQ ID NO. 3), were synthesized as follows. Peptides were synthesized by the solid-phase method utilizing an automated synthesizer (Applied Biosystems, Inc. Model 431A) (see Stewart and Young, In *Solid Phase Peptide Synthesis,* 2nd ed. (Pierce Chemical Co., Rockford, Ill., 1984), which is incorporated herein by reference). The peptides, having a C-terminal amide, were synthesized using p-methlybenzhydrylamine (pMBHA) resin. Peptides having a C-terminal acid can be synthesized using, for example, a chloromethylated resin. Peptides having an N-terminal acetyl group were acetylated using a mixture of acetic anhydride (20 eq) and diisopropylethylamine (20 eq) in N-methylpyrrolidone.

N-terminal tertbutyloxycarbonyl (Boc) protection was employed for all amino acids. Dicyclohexylcarbodiimide and hydroxybenzyltriazole were used in the coupling reactions. The extent of the reactions was monitored using the standard ninhydrin test.

Following synthesis, the peptides were removed from the resin and deprotected by adding anhydrous hydrogen fluoride (HF; 10 ml/g of resin-bound peptide) containing anisole (1 ml/g) at 0° C. for 60 min. The HF was removed by evaporation and the residue was washed with anhydrous ether. The crude peptides were extracted with water or 15% aqueous acetic acid and the aqueous fractions were combined and cyclized as described below.

The crude acyclic peptide was dissolved in 0.1M ammonium bicarbonate (0.5 mg/ml) and stirred uncovered. The course of the reaction was monitored by HPLC. After cyclization was complete (several hours to several days), the solution was filtered and the peptides were purified and characterized as described below.

B. Synthesis of cyclic peptides having lactam bridges:

Cyclic peptides which have a lactam bridge, such as (Nle)GD(Y-OMe)RE-NH$_2$ (SEQ ID NO. 4), can be synthesized as outlined here. The protected peptide resin can be synthesized using the pMBHA resin. The lactam bridge is formed while the peptide is still on the resin using the method described by Felix et al., *Int. J. Pept. Prot. Res.* 31:231 (1988) and by Felix et al., *Int. J. Pept. Prot. Res.* 32:441 (1988), each of which is incorporated herein by reference.

Essentially, the method of Felix et al. uses Nc-Boc-amino acids together with 9-fluorenylmethyl ester (OFm) side-chain protection. Asp and Glu are introduced using Boc-Asp(OFm)-OH and Boc-Glu(OFm)-OH. After coupling the final amino acid, OFm protecting groups are selectively removed by treating the peptide resin with 50% piperidine in dimethylformamide for 1 hr. The peptide resin is then washed with 3×40 ml dichloromethane and mixed with a 6-fold excess of BOP reagent (benzotriazol-1-yl-oxy-tris (dimethylamino)phosphonium hexafluorophosphate) in the presence of an 8-fold excess of diisopropylethylamine for 5 hr. Coupling reactions are repeated until the resin gave the negative ninhydrin test.

After the cyclization reaction is complete, peptides are removed from the resin and deprotected using anhydrous HF (10 ml/g of resin-bound peptide) containing anisole (1 ml/g) at 0° C. for 60 min. The HF is removed by evaporation and the residue washed with anhydrous ether. The crude peptides are then extracted with water or 15% aqueous acetic acid and the aqueous fractions combined, lyophilized, purified and characterized as described below.

C. Purification and Characterization of the Peptides

The crude peptides were purified via preparative RP-HPLC on a C$_{18}$ silica gel column (Waters Delta-Pak, 15 μm, 300 A, 47×300 mm) eluting with a linear acetonitrile gradient (0–30%) with a constant concentration of trifluoroacetic acid (TFA; 0.1%, v/v) over 30 min at a flow rate of 40 ml/min. The purified peptides were analyzed by analytical RP-HPLC using a C-18 column (Vydac, 5 μm, 300 A, 4.5×250 mm). The purified peptides were recovered by lyophilization of the HPLC fractions and were at least 950 pure. For analytical HPLC, a binary solvent system, water containing 0.1% TFA and acetonitrile containing 0.1% TFA as the organic modifier, was used. The solvent programs involved linear gradients as follows: (1) 10–45% acetonitrile over 35 min with a flow rate of 1.5 ml/min and (2) 0–70% acetonitrile over 30 min with flow rate of 1.5 ml/min.

In some cases, the peptide can be adjusted to a neutral pH and potassium ferricyanide added to the TFA peptide to minimize polymerization that might result due to the presence of the reducing agent. The potassium ferricyanide is removed by ion exchange chromatography and the peptides were lyophilized. The presence of thiol reducing agents, which indicates the need to add potassium ferricyanide, can be detected using Ellman's test (*Arch. Biochem. Biophys.* 82: 70 (1959), which is incorporated herein by reference).

To confirm the correct amino acid sequences were synthesized, the peptides were characterized by fast atom bombardment mass spectroscopy and by amino acid analysis. Amino acid analysis was performed on a Pickering Labs-Trione amino acid analyzer that was equipped with spectra-physics UV detector. Hydrolysis of peptide samples for amino acid analysis was performed on 1 mg samples with 1 ml constant boiling 6N HCl. Samples were degassed, sealed under vacuum and heated for 24 hr. at 110° C.

EXAMPLE II

Platelet Aggregation

This example provides platelet aggregation studies for various peptides of the present invention. The studies compare the effect of the peptide on aggregation in both citrated and heparinized plasma. Because citrate is a chelating agent for calcium ions, the citrated plasma has a low calcium concentration as is characteristic of a clot site. In contrast, heparinized plasma has a calcium concentration similar to that of physiological conditions elsewhere in the blood stream.

Whole blood was drawn by a licensed phlebotomist from the antecubital vein using a 21 gauge butterfly infusion set and syringe from normal human volunteers. Platelet-rich plasma (PRP) was prepared by centrifuging heparinized (20 Units lithium porcine mucosa heparin/ml whole blood) or citrated (0.38% sodium citrate) whole blood for 12 min. at 200 relative centrifugal force (RCF). Platelet-poor plasma (PPP) is prepared by centrifuging PRP at 750 RCF for 12 min. and collecting the supernatant. Blood cell counts were performed using a Serano Baker automated cell counter. PRP platelet counts were adjusted to 200,000/μl by dilution with PPP. Final plasma free Ca+$^2$ concentrations were approximately 0.18 mM for citrated plasma and 2.3 mM for heparinized plasma. Platelet aggregation was determined spectrophotometrically utilizing a four channel aggregometer (Chrono-Log 570) by measuring the increase of light transmission through a stirred suspension of PRP maintained at 37° C. Dilutions of the peptides were added to the suspensions and aggregation induced with 10 μM adenosine diphosphate (ADP). Values were expressed as percentage of aggregation in the absence of peptides. This represents the percentage of light transmission standardized to PRP and PPP samples yielding 0% and 100% light transmission respectively.

Peptide anti-aggregation potencies were determined from dose-responsive curves for the inhibition of the maximum aggregation responses stimulated by high doses of ADP (10

μm). The 50% inhibitory concentration of each peptide (IC$_{50}$) was determined by regression analysis of these curves.

Peptides of the present invention which were tested using the above procedures include Ac-CNPAGD(Y-OMe)RC-NH$_2$ (SEQ ID NO. 2), Ac-CNP(Nle)GD(Y-OMe)RC-NH$_2$ (SEQ ID NO. 3) and (Nle)GD(Y-OMe)RE-NH$_2$(SEQ ID NO. 4). In addition, control peptides tested were as follows: the linear peptide GRGDSP (SEQ ID NO. 7), the linear counterpart to the peptide of SEQ ID NO. 2, Ac-CNPAGD(Y-OMe)RC-NH$_2$ (SEQ ID NO. 5), the linear counterpart to the peptide of SEQ ID NO. 3, Ac-CNP(Nle)GD(Y-OMe)RC-NH$_2$ (SEQ ID NO. 6), and Ac-CNPRGD(Y-OMe)RC-NH$_2$ (SEQ ID NO. 8).

Figure 1:
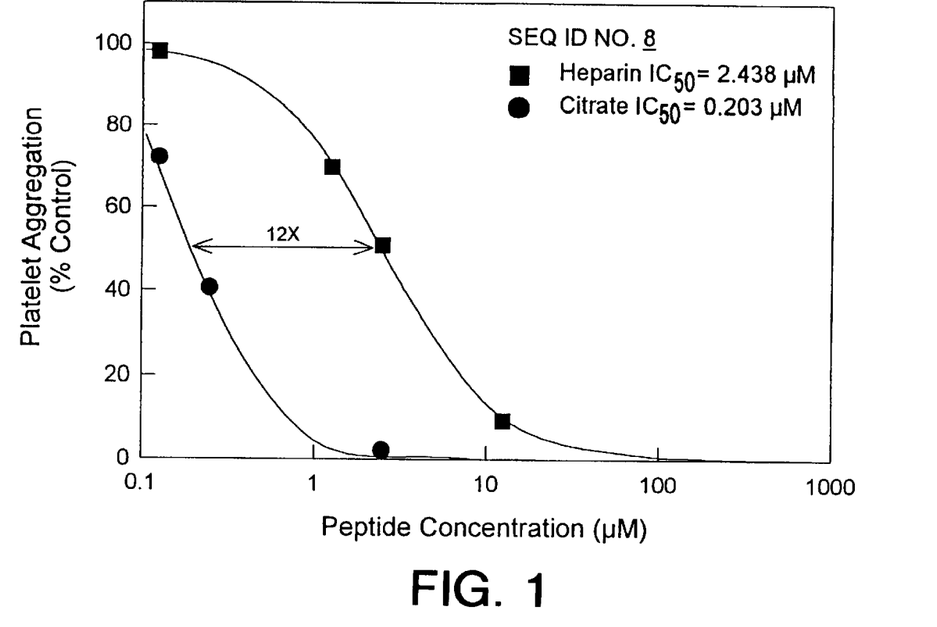
FIG. 1 shows the percentage of platelet aggregation in citrated plasma (low $Ca^{+2}$ concentration) and heparinized plasma (physiological $Ca^{+2}$ concentration) in the presence of a control peptide, Ac-CNPRGD(Y-OMe)RC-$NH_2$ (SEQ ID NO. 8).
Figure 2A:
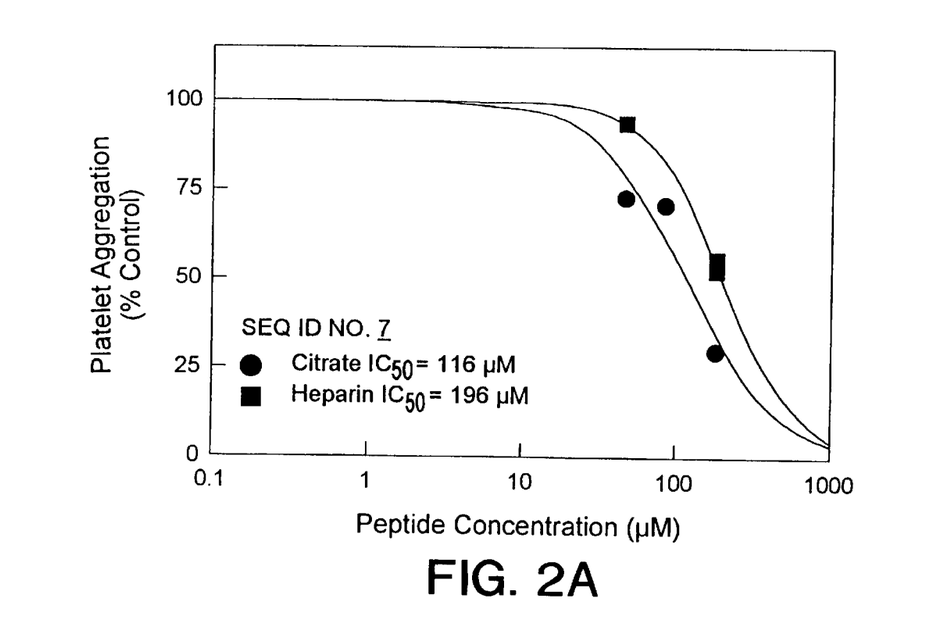
Figure 2B:
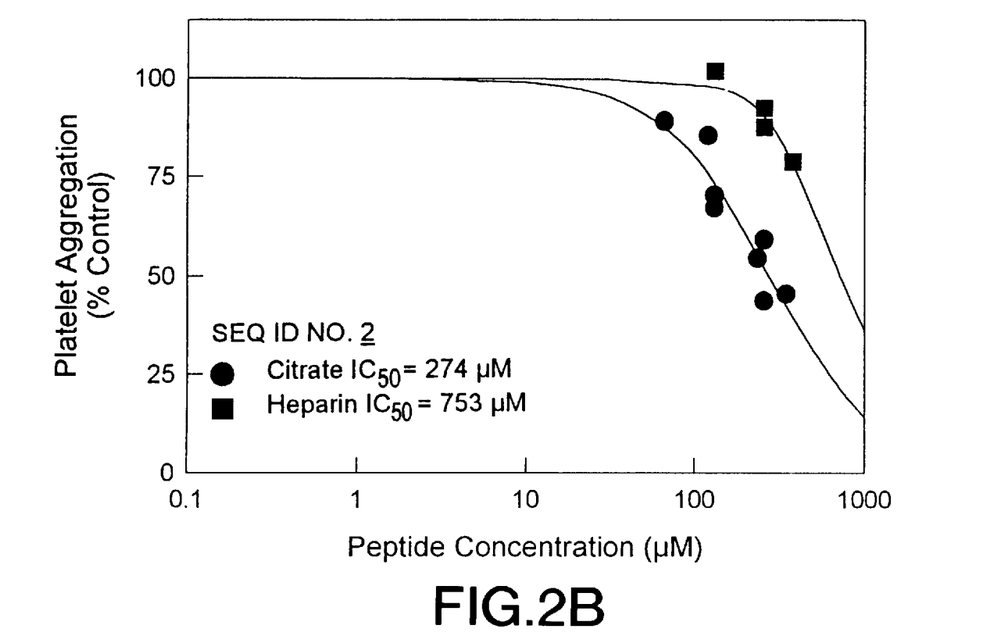
Figure 2C:
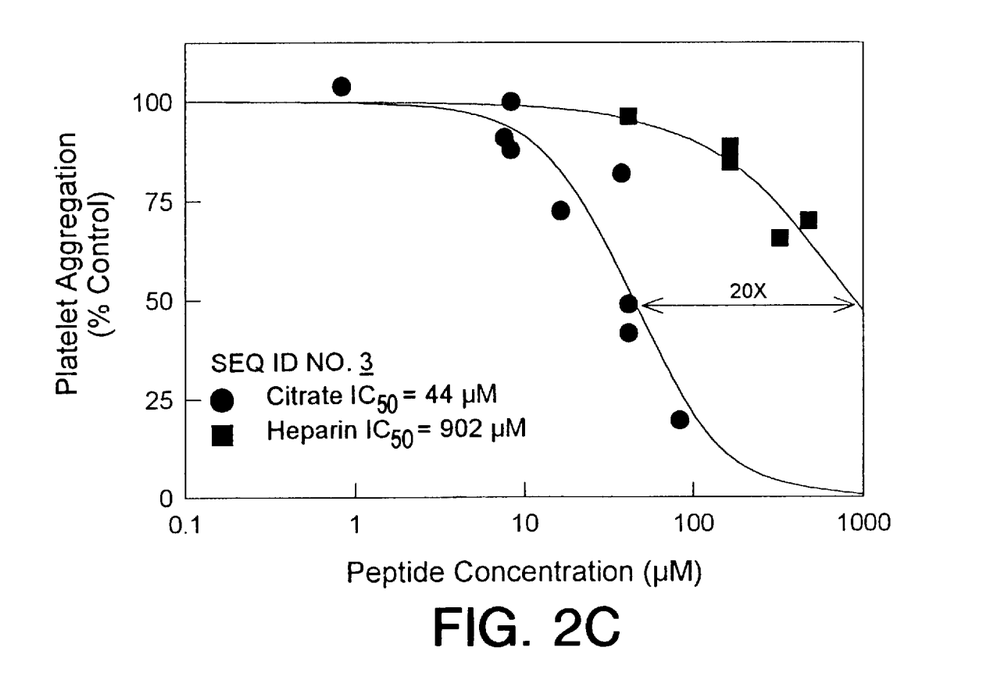
Figure 3:
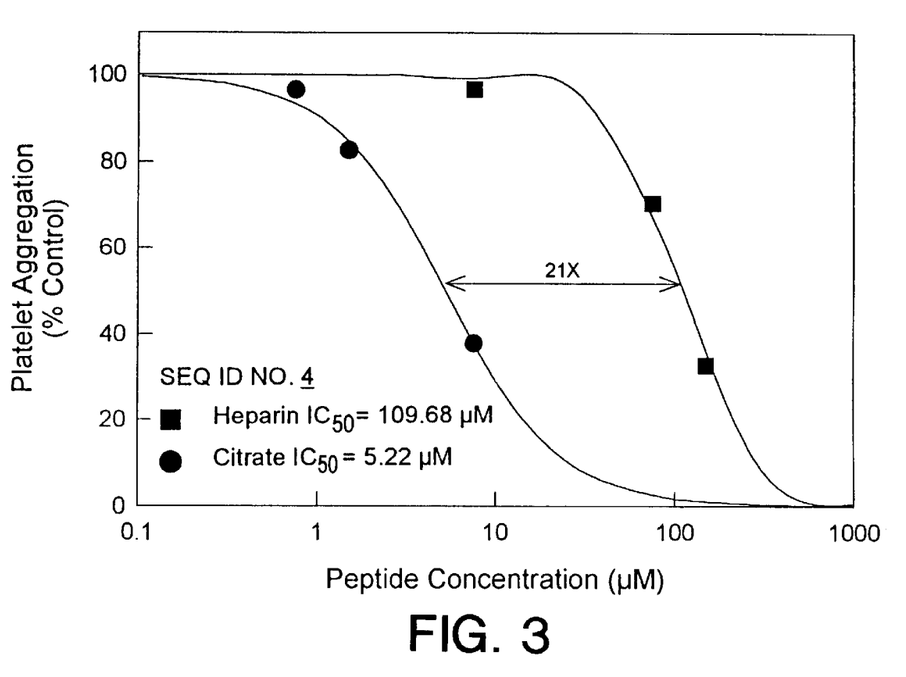
FIG. 3 also provides the percentage of platelet aggregation in citrated and heparinized plasma with another peptide of the present invention, (Nle)GD(Y-OMe)RE-$NH_2$ (SEQ ID NO. 4).

The results of these experiments are provided in FIGS. 1 to 3 and Table I. As shown in these Figures and the Table, each of the peptides tested have inhibitory effects on platelet aggregation stimulated with ADP. However, as shown in FIGS. 1 to 3 not all peptides are equal with respect to their apparent binding affinity for GP-IIb/IIIa in low calcium concentration versus physiological calcium concentration. In fact, as shown in FIG. 2a, the linear control peptide GRGDSP (SEQ ID NO. 7) exhibits essentially the same apparent binding affinities regardless of the calcium concentration. In contrast, FIG. 2b clearly shows a separation between the apparent binding affinity of Ac-CNPAGD(Y-OMe)RC-NH$_2$ (SEQ ID NO. 2) for GP-IIb/IIIa at low (citrate) and higher (heparin) calcium concentrations. The peptide Ac-CNP(Nle)GD(Y-OMe)RC-NH$_2$ (SEQ ID NO. 3) exhibits a 20-fold increase in apparent affinity for GP-IIb/IIIa in low calcium concentration as compared to physiological calcium concentration. This 20-fold increase is unexpectedly superior as compared to the 12-fold increase exhibited with the control peptide Ac-CNPRGD(Y-OMe)RC-NH$_2$ (SEQ ID NO. 8) (shown in FIG. 1). As well, another peptide of the present invention, (Nle)GD(Y-OMe)RE-NH$_2$ (SEQ ID NO. 4), provides a 21-fold separation in its apparent affinity for GP-IIb/IIIa in low calcium concentration over physiological calcium concentration.

The 50% inhibitory concentration of each peptide (IC$_{50}$) is provided in Table I. As can be seen from the Table, the linear counterparts to the peptides corresponding to SEQ ID NOs. 2 and 3, Ac-CNPAGDC(Y-OMe)RC-NH$_2$ (SEQ ID NO. 5) and Ac-CNP(Nle)GD(Y-OMe)RC-NH$_2$ (SEQ ID NO. 6), respectively, have little to no activity. More importantly, these linear peptides, as compared to those of the present invention, exhibit no difference in their apparent affinity for GP-IIb/IIIa at low versus higher calcium concentration.

TABLE I

PLATELET AGGREGATION IN CITRATED PLASMA

| SEQ ID NO. | STRUCTURE | SEQUENCE | IC$_{50}$ (μg/ml) |
|---|---|---|---|
| 2 | Cyclic | Ac-CNPAGD(Y-OMe)RC-NH$_2$ | 309 |
| 5 | Linear | Ac-CNPAGD(Y-OMe)RC-NH$_2$ | >370 |
| 3 | Cyclic | Ac-CNP(Nle)GD(Y-OMe)RC-NH$_2$ | 43 |
| 6 | Linear | Ac-CNP(Nle)GD(Y-OMe)RC-NH$_2$ | >370 |
| 8 | Cyclic | Ac-CNPRGD(Y-OMe)RC-NH$_2$ | 0.2 |

The data provided herein evidences that the subject peptides are useful antithrombotic agents. Importantly, peptides of the present invention have a higher apparent affinity for GP-IIb/IIIa at low calcium concentration as compared to GP-IIb/IIIa at higher calcium concentration. Peptides of the present invention would inhibit platelet aggregation only at the site of a clot and not throughout the whole blood stream. Therefore, peptides of the present invention, while decreasing aggregation at a clot site would not affect normal platelet functions and would, thereby, reduce the bleeding complications typical of other thrombotic agents.

All journal article and reference citations provided above, in parentheses or otherwise, whether previously stated or not, are incorporated herein by reference.

Although the invention has been described with reference to the Examples provided above, it should be understood that various modifications can be made without departing from the spirit of the inventions. Accordingly the invention is limited only by the claims.

We claim:

1. A cyclic peptide having the structure:

$$Y-X_1-X_2-G-D-X_3-X_4-X_5-Z$$

(SEQ ID NO. 1), wherein:

$X_1$ and $X_5$ are independently each zero to five amino acids;

$X_2$ and $X_3$ are independently each a hydrophobic amino acid;

$X_4$ is a positively charged amino acid;

Y is selected from the group consisting of a hydrogen atom, $COCH_3$, CO-alkyl, an alkyl group, $CH_2PH$, COPh, $COOCH_2Ph$ and COO-alkyl; and Z is selected from the group consisting of OH, $NH_2$, $NH-NH_2$, O-alkyl, SH, S-alkyl, NH-alkyl and $NHCH_2Ph$, provided that the peptide is cyclized through a bridge between two amino acids, excluding the G, D and $X_3$ amino acids in the formation of the bridge.

2. The peptide of claim 1, wherein the hydrophobic amino acid for either, or both, $X_2$ and $X_3$ is selected from the group consisting of Ala, Val, Ile, Leu, Phe, Tyr, Trp, a Tyr derivative, a Phe derivative, Nle, Nve, Cha, Nap, 2-Nal and Cit.

3. The peptide of claim 1, wherein $X_2$ is selected from the group consisting of Ala, Val, Ile, Leu, Phe, Tyr, Trp, Nve, Nle, Cha and Nap.

4. The peptide of claim 3, wherein $X_2$ is selected from the group consisting of Ala, Leu and Nle.

5. The peptide of claim 1, wherein $X_3$ is selected from the group consisting of Phe, a Phe derivative, Tyr, a Tyr derivative and Trp.

6. The peptide of claim 5, wherein $X_3$ is Tyr-OMe.

7. The peptide of claim 1, wherein the positively charged amino acid of $X_4$ is selected from the group consisting of Arg, Lys, His, Orn and homArg.

8. The peptide of claim 7, wherein $X_4$ is Arg.

9. The peptide of claim 1, wherein both $X_1$ and $X_5$ are independently each one to five amino acids, provided that one of the amino acids for each $X_1$ and $X_5$ is an amino acid capable of forming a cyclization of the peptide.

10. The peptide of claim 9, wherein one of the amino acids capable of forming a bridge for each of $X_1$ and $X_5$ is independently selected from the group consisting of Cys, Pen, Mpa, Pmp, Pmc and Pas.

11. The peptide of claim 1, wherein the peptide is cyclized through a bridge between two amino acids which bridge is between the two amino acids, collectively, selected from the group consisting of $X_1$ and $X_5$, $X_1$ and $X_4$, $X_2$ and $X_5$, and $X_2$ and $X_4$.

12. A peptide having one of the following sequences:

Ac-<u>CNPAGD(Y-OMe)RC</u>-$NH_2$ (SEQ ID NO. 2);

Ac-<u>CNP(Nle)GD(Y-OMe)RC</u>-$NH_2$ (SEQ ID NO. 3); and

<u>(Nle)GD(Y-OMe)RE</u>-$NH_2$ (SEQ ID NO. 4).

13. A composition of matter comprising the peptide of claim 1 and a physiologically acceptable carrier.

14. A method of preventing thrombosis, comprising administering a therapeutically effective amount of a peptide of claim 1 in a physiologically acceptable carrier.

15. A method of preventing a thrombotic condition, comprising administering a therapeutically effective amount of a peptide of claim 1 in a physiologically acceptable carrier.

16. The method of claim 15, wherein the thrombotic condition is selected from the group consisting of stroke, myocardial infarction, vascular graft occlusion, unstable angina and abrupt reclosure following angioplasty.

17. A method of treating thrombosis, comprising administering a therapeutically effective amount of a peptide of claim 1 in a physiologically acceptable carrier.

18. A method of treating a thrombotic condition, comprising administering a therapeutically effective amount of a peptide of claim 1 in a physiologically acceptable carrier.

19. The method of claim 18, wherein the thrombotic condition is selected from the group consisting of stroke, myocardial infarction, vascular graft occlusion, unstable angina and abrupt reclosure following angioplasty.

\* \* \* \* \*

UNITED STATES PATENT AND TRADEMARK OFFICE
CERTIFICATE OF CORRECTION

PATENT NO. : 5,858,972
DATED : January 12, 1999
INVENTOR(S) : Pierschbacher et al.

Page 1 of 1

It is certified that error appears in the above-identified patent and that said Letters Patent is hereby corrected as shown below:

Column 2,
Line 16, please delete "SUMMARY THE" and replace with -- SUMMARY OF THE --.

Column 3,
Line 39, please delete "Leudine" and replace with -- Leucine --.

Column 5,
Line 5, please delete "in higher" and replace with -- higher --.

Column 11,
Line 40, please delete "Nc-Boc-amino" and replace with -- $N^{\alpha}$-Boc-amino --.

Column 12,
Line 3, please delete "950" and replae with -- 95% --.

Column 21, claim 1,
Line 35, please delete "NHCH$_2$Ph," and replace with -- NHCH$_2$PH, --.

Signed and Sealed this

Second Day of April, 2002

Attest:

JAMES E. ROGAN
*Attesting Officer*     *Director of the United States Patent and Trademark Office*